United States Patent [19]

Kanner

[11] Patent Number: 5,607,392
[45] Date of Patent: Mar. 4, 1997

[54] FIXED NEEDLE CONNECTOR FOR IV ASSEMBLY AND METHOD OF ASSEMBLING

[75] Inventor: Rowland W. Kanner, Guntersville, Ala.

[73] Assignee: Ryder International Corporation, Arab, Ala.

[21] Appl. No.: 372,291

[22] Filed: Jan. 13, 1995

[51] Int. Cl.$^6$ .................................................. A61M 37/00
[52] U.S. Cl. ........................ 604/86; 604/88; 604/283; 604/905; 128/898
[58] Field of Search ........................ 604/283, 284, 604/905, 411, 415, 192, 86, 88, 263, 264; 128/898

[56] References Cited

U.S. PATENT DOCUMENTS

| | | | |
|---|---|---|---|
| 4,511,359 | 4/1985 | Vaillancourt . | |
| 5,120,324 | 6/1992 | Sancoff | 604/283 |
| 5,139,483 | 8/1992 | Ryan | 604/905 X |
| 5,207,667 | 5/1993 | Walker et al. | 604/905 |
| 5,376,073 | 12/1994 | Graves et al. | 604/283 X |

OTHER PUBLICATIONS

*Interlink® I.V. Access System* brochure, Baxter Healthcare Corporation, 1993.

*Primary Examiner*—John D. Yasko
*Attorney, Agent, or Firm*—Trexler, Bushnell, Giangiorgi & Blackstone, Ltd.

[57] ABSTRACT

A needle connector assembly for attachment to an IV receptacle which includes a needle hub with a cannula or needle attached thereto and a housing to which the needle hub is mounted. The hub has a plurality of equi-spaced splines thereon and the housing has an aperture in the rear portion thereof defining a plurality of equi-spaced slots therein which mate with the splines when the hub and the housing are secured together. Along the length of the interchangeable splines and slots, an inwardly projecting, one-way barb is provided which has an inclined or cam surface at its leading edge. When the hub is inserted into the housing, the needle is completely surrounded by the housing and the barbs bite into the adjacent material to preclude withdrawal of the hub from the housing. The housing and the receptacle may interlock with each other at a patient IV site to secure the housing to the receptacle.

31 Claims, 3 Drawing Sheets

5,607,392

FIXED NEEDLE CONNECTOR FOR IV ASSEMBLY AND METHOD OF ASSEMBLING

BACKGROUND OF THE INVENTION

This invention is generally directed to a novel connector assembly construction and a novel design for the components which provide for a novel method of assembling such a connector assembly. The connector assembly provides an intravenous ("IV") connection between an IV tube which is attached to a patient and a second IV tube which is attached to a supply of intravenous fluid, including medicines or the like. The connector assembly includes a housing in which a needle or cannula is secured with said needle or cannula being surrounded by a housing. The connector assembly, viz., the cannula and housing, are assembled to a needle site receptacle which is in turn connected to the patient's IV supply line. More particularly, the invention contemplates a novel connector assembly which is connected to an IV receptacle to provide a safe, sealed connection. The connector assembly is assembled to the receptacle easily and minimizes the possibility of a nurse or technician who is assembling the connection from being inadvertently punctured by the needle or cannula.

The connector assembly of the present invention can be manufactured and assembled inexpensively, quickly and easily. In this regard a needle carrying hub is force-fitted into the housing to form the assembled device and cannot be easily removed from the housing. One-way barbs are employed to bite into the needle hub or the housing to preclude withdrawal of the needle hub from the housing. Thus, expensive molds and over molding or insert molding processes are not required.

Prior art connector assemblies, such as the Interlink® I.V. Access System provides a connection between an IV tube which is attached to a patient and a second IV supply tube which is attached to a supply of intravenous fluids, including medicines or the like. Interlink® is a registered trademark of the Baxter Healthcare Corporation. The Interlink® system includes a connector component including a cannula which is inserted into a receptacle carried by the patients IV line, and the component also includes a pair of locking levers on either side of the cannula. To form the connection, a nurse or technician presses on the levers so that the distal ends of the levers pivot outwardly. He or she next inserts the cannula into an injection site receptacle member which is attached to the patient's IV tube. Thereafter, the levers are released and the distal ends of the levers grip the injection site member to maintain the connection.

This type of system provides an effective connection for delivering medicines to a patient. In this type of system, however, the tip of the cannula is uncovered and exposed. Thus, a nurse or technician can inadvertently contact the cannula end and puncture himself or herself which can result in contamination of the sterility of the IV line or injury to the nurse or technician.

It is also known to provide a connector assembly, comprised of a housing and a needle carrying hub mounted within the housing, wherein the hub is disposed through the open forward end of the housing. That is, the forward end is the end of the housing that receives or is initially engaged with the IV receptacle. This design requires a cumbersome and expensive procedure of disposing and aligning the needle hub within the housing, and the employment of some form of attachment procedure for securing the hub within the housing. A further disadvantage with this design, is that the fluid must first enter the housing, then pass into the needle hub, and from the needle hub into the receptacle. This design thus presents numerous interfaces between the various components, which interfaces are potential sources of leakage. It will be appreciated from the discussion which follows, the present invention minimizes the number of interfaces.

The present invention overcomes many of the prior art problems by providing a housing which completely surrounds the cannula, including the tip of the cannula, and which can be assembled easily, quickly and does not require anything more than the initial engagement of the needle carrying hub with the housing. Also assembly is effected through the rear portion of the housing with a minimum degree of skill and without complicated assembly techniques. Further, there is provided a connection assembly wherein the needle or cannula is surrounded by the housing thus reducing the possibility of a nurse or technician being inadvertently punctured during use, ie. assembly of the cannula to a receptacle.

The present invention presents several other advantages over prior art connector assemblies as will be described herein.

OBJECTS AND SUMMARY OF THE INVENTION

A general object of the present invention is to provide a novel needle connector assembly or device construction and method of assembling such a device.

Another object of the present invention is to provide a needle connector assembly or device which is attached to a receptacle to provide a safe, sealed connection for intravenous ("IV") lines.

A further object of the present invention is to provide a needle connector assembly or device which shields an IV cannula or needle preparatory to insertion into an IV line or a receptacle.

Another object of the present invention is to provide a novel needle connector assembly which is easily and securely assembled.

Yet another object of the present invention is to provide a needle connector assembly which includes a hub having a cannula or needle at an end thereof which can be inserted into but cannot be withdrawn from a housing.

A further object of the present invention is to provide a needle connector assembly which minimizes the possibility of a nurse or technician from being punctured by a cannula or needle either before or after use.

A specific object of the present invention to provide a needle connector assembly which includes a hub for mounting a needle or cannula that uses a reduced amount of plastic material while maintaining strength.

Briefly, and in accordance with the foregoing, the present invention discloses a novel needle connector assembly which provides a safe, sealed connection between an IV tube which is attached to a patient and an IV supply line which is attached to a supply of intravenous fluids, including medicines or the like. The assembly includes a needle or cannula carrying hub and a housing which are secured together. The hub and the housing are connected to a needle site receptacle or connector member with the needle or cannula inserted through a plug capped by the receptacle, which receptacle is in turn connected to the patient's IV supply line.

The hub has a cannula or needle secured to one end thereof and has a plurality of equi-spaced, male splines at its opposite end. A plurality of equi-spaced slots are provided on the hub which alternate with the splines.

The housing is a generally cylindrical member with an internally splined portion at a rearward end thereof. Note: the forward end of the housing is the end into which the receptacle is received or engaged: the opposite end is termed the rearward end of the housing. The splined portion includes a plurality of equi-spaced slots which alternate with a plurality of equi-spaced inwardly projecting splines. In the preferred, illustrated embodiment, each of the slots has an inwardly projecting, one-way barb along its length. Each barb has an inclined or cam surface which permits and facilitates insertion of the needle hub into the housing and a truncated surface which prevents removal of the hub from the housing once the hub has been inserted. At the housing's opposite or forward end, the housing has means for interlocking the needle site receptacle thereto. While the preferred, illustrated form of the invention involves barbs on the wall surfaces of the housing slots, it is envisioned that the one-way barbs could be employed on the hub slots, or on either the hub or housing splines. Also, means other than the one-way barbs could be used to maintain assembly once initially attained, such as a tapered wedge lock, or if desired, gluing or a form of ultrasonic welding.

The needle site receptacle is a generally cylindrical member which has at least one pin which projects outwardly therefrom. The pin is inserted within the slot or aperture on the housing to connect the housing and the receptacle together. A rubber plug is provided at one end of the receptacle through which the cannula or needle is engaged to provide a fluid path from the interior of the connector assembly to the interior of the receptacle.

To assemble the cannula or needle carrying hub and housing together, the hub is force fit into the housing. The inwardly projecting one-way barbs permit the male splines on the hub to enter the housing but upon any attempt to withdraw the hub, the barbs on the housing bite into the males splines on the hub to preclude withdrawal of the hub from the housing and the splines on the housing are effectively locked within the slots on the hub. When assembled, the cannula or needle is completely surrounded by the housing.

To use the assembled hub and housing with a patient to provide a connection to a supply, the housing is interlocked with the receptacle. The end of the receptacle is inserted into the housing with the pin sliding along the length of the slot in the housing. The cannula or needle on the hub penetrates through the receptacle's rubber plug. The present invention discloses two embodiments for interlocking the receptacle and the housing.

In a first embodiment, the slot in the housing has a restricted portion which has a width which is slightly smaller than the diameter of the pin on the receptacle. When the pin is inserted into the slot to connect the receptacle and the housing together, the pin passes beyond the restricted portion in the slot to securely hold the pin within the slot and to lock the housing and the receptacle together. The slot has a first portion which is generally collinear with the center line of the housing and a second portion which is generally perpendicular to the center line of the housing and to the first portion of the slot. The restricted portion is along the second portion.

In a second embodiment, the housing includes an integral, spring latch which overlays the slot. The latch has an aperture along its length. The latch is movable away from the cylindrical housing to expose the slot. To connect the receptacle and the housing together, the resilient latch is moved away from the housing and thereafter, the pin on the receptacle is inserted into the slot on the housing. Next, the latch is moved towards the housing and the pin is captured within the aperture in the latch to securely hold the pin within the slot and to lock the housing and the receptacle together.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE PREFERRED EMBODIMENT

While the invention may be susceptible to embodiment in different forms, there is shown in the drawings, and herein will be described in detail, specific preferred embodiments with the understanding that the present disclosure is to be considered an exemplification of the principles of the invention, and is not intended to limit the invention to that as illustrated and described herein.

As shown in the drawings, the present invention presents a novel IV connection assembly 20. The IV connection assembly 20 includes a needle carrier or connector assembly or device 22 which is operatively connected to a needle site receptacle or connector element 24. The connector assembly 22 includes a needle hub 26 having a cannula or a needle 28 secured thereto and a needle hub housing 30. The IV connection assembly 20 provides a safe, sealed connector system for intravenous ("IV") lines and shields the needle 28 preparatory to insertion into an IV line or the receptacle.

Figures 1, 2, 3, 3A:
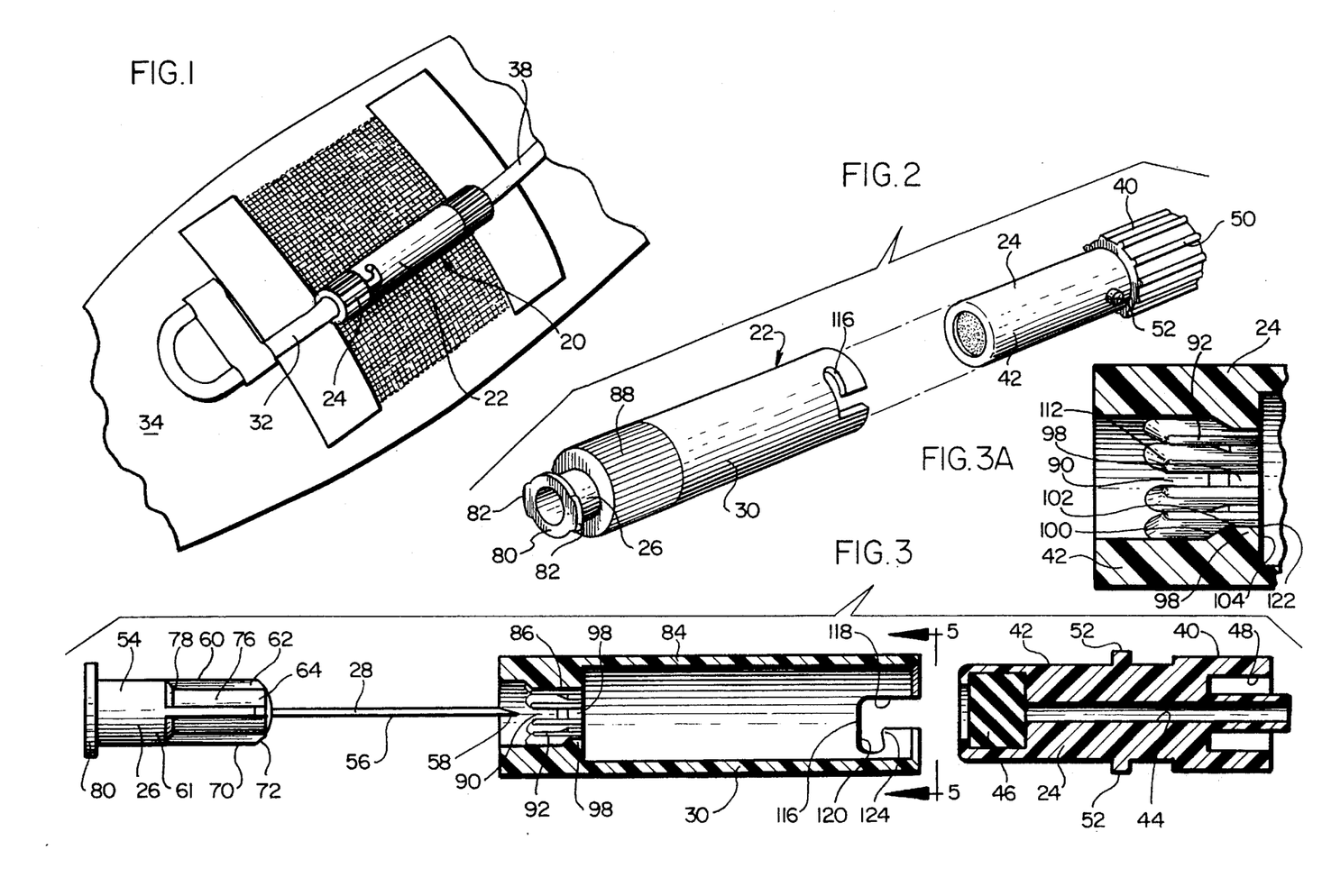
FIG. 1 is a perspective view of a needle connector assembly which incorporates the features of a first embodiment of the invention shown in use with a patient.
FIG. 2 is a perspective view of the needle connector assembly shown in FIG. 1 prior to interconnection to the patient's IV line.
FIG. 3 is an exploded view of the needle connector assembly shown in FIG. 1 which is formed of a needle hub; a needle hub housing and a needle site receptacle; the housing and receptacle being shown in a cross-sectional view and the needle hub being shown in side elevation; the needle hub housing and needle hub being shown along line 3—3 of FIG. 5.
FIG. 3A is an enlarged view of a portion of the needle hub housing shown in FIG. 3 to more clearly show an internally splined portion of the housing.

As shown in FIG. 1, IV connection assembly 20 and its associated elements are used to administer intravenous fluids, including medicines, to a patient. A short IV tube or line 32 has an end which is affixed to the patient 34 by known means. The opposite end of the IV line 32 is connected to a first end of the receptacle 24. The second end of the receptacle 24 is connected to a first or forward end of the needle connector device 22 by means described herein. A second end of the receptacle 24 is connected to a conventional Luer lock fitting 36 (not shown in FIG. 1, see FIGS. 4 and 9) which is in turn connected to an IV supply tube or line 38 that is connected to a supply (not shown) of fluids. The Luer lock fitting 36 is of a conventional structure and, as such, is not described herein.

The needle site receptacle 24 includes an outer plastic housing having a first portion 40 and a second portion 42. The first portion 40 is larger than the second portion 42 for reasons described herein. The receptacle 24 has a passageway 44 therethrough generally along the center line thereof. A rubber stopper or plug 46 is mounted within the second portion 42 of the receptacle 24 in an enlarged portion of the passageway 44 proximate to one end of the receptacle 24. The rubber plug 46 seals the end of the receptacle 24 and prevents the flow of fluids through the passageway 44 in the receptacle 24. When the rubber plug 46 is penetrated by the cannula or needle 28 attached to the hub 26 as described herein, a passageway is provided through the rubber plug 46 and thus, fluids can pass into and through the receptacle 24 to the patient line 32.

Figure 4:
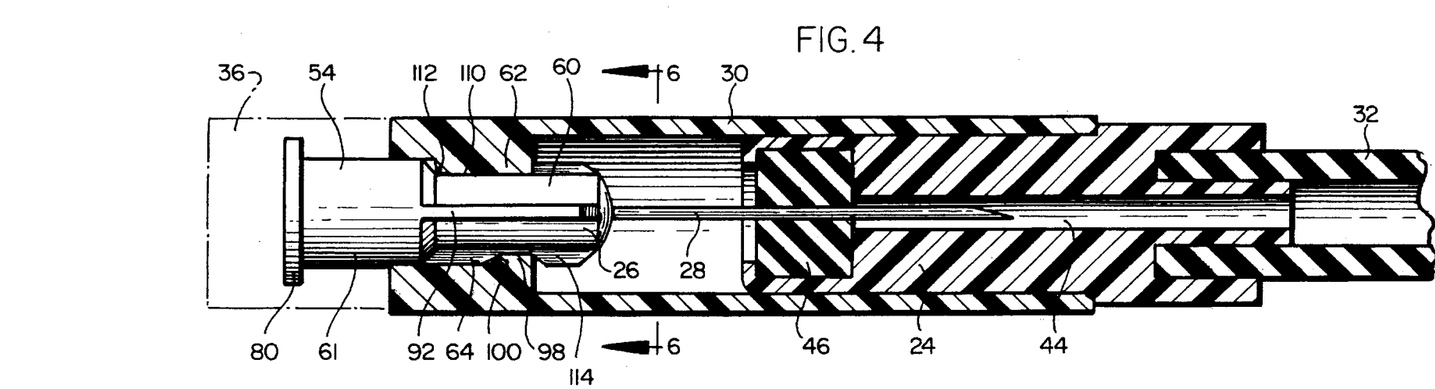
FIG. 4 is an assembled view of the needle connector assembly shown in FIG. 3.
Figure 9:
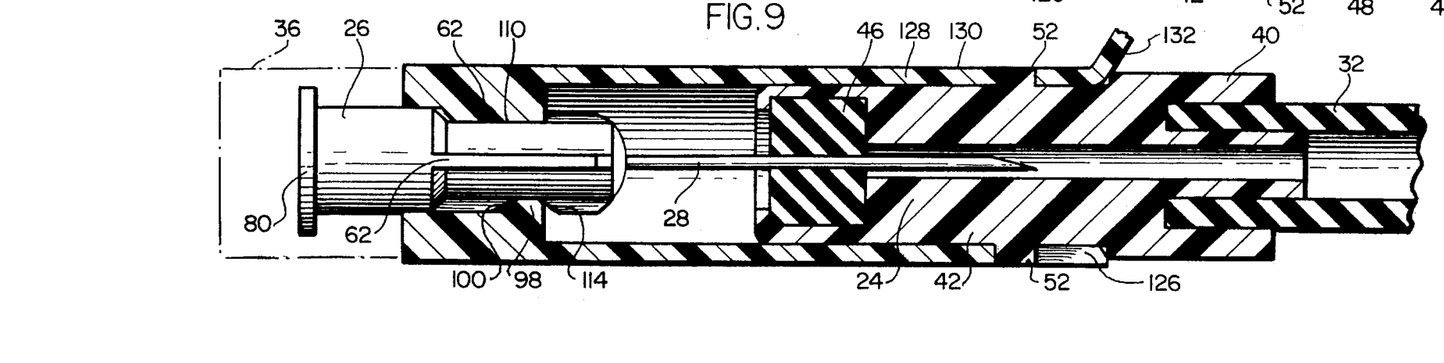
FIG. 9 is an assembled view of the needle connector assembly shown in FIG. 8.

At the first end of the receptacle 24, as shown in FIGS. 4 and 9, a circular recess 48 is provided for connecting the IV tube 32 to the receptacle 24. The circular recess 48 is radially spaced from the end of the passageway 44 so as to not interfere with the passageway 44. The exterior surface of the first portion 40 of the receptacle 24 includes raised ridges or ribs 50 thereon so that a nurse or technician can easily handle the receptacle 24 during assembly of the needle connector device 22 thereto as described herein.

The second portion 42 of the receptacle has two posts or pins 52 which project outwardly from the first portion 40 and are diametrically opposed from each other on the circumference of the first portion 40. The pins 52 are used to interlock the needle site receptacle 24 to the assembled connector device 22 as described herein. While two pins 52 are shown in drawings, it is to be understood that more pins may be used to interlock the receptacle 24 and the device 22 together, or that alternate locking means may be employed. Also, the construction of the receptacle 24 as shown in the drawings and discussed above is a preferred form. It should be noted however that the specific design of the receptacle may vary, without departing from the present invention.

The needle hub 26 is formed from a plastic carrier portion 54 which has the cannula or needle 28 integrally secured to an end thereof. Preferably, the needle 28 is glued to the hub 26. Where the cannula 28 is a plastic material, such cannula 28 can be molded integrally with the hub 26. Alternatively, to integrally connect the hub 26 and the needle 28 together, the carrier portion 54 can be injection molded around the end of the needle 28, a technique referred to in the art as insert molding. The needle 28 is of a conventional structure which includes an elongate body 56 having a passageway (not shown) therethrough so that fluids can pass through the needle 28, and a tip 58 at the end of the needle 28 opposite to the one secured to the hub 26. The tip 58 can be sharpened or can be relatively blunt so long as the tip 58 can penetrate through the rubber plug 46 in the receptacle 24 as described herein. The needle 28 may be made of a suitable, rigid material, such as plastic or stainless steel.

The plastic carrier portion 54 of the hub 26 has a first generally cylindrical body portion 60 with a plurality of equi-spaced, male splines 62 around the circumference of the body portion 60 and a second larger cylindrical body portion 61. The splines 62 are integrally formed with the body portion 60 and project outwardly therefrom. Preferably, the splines 62 are disposed 90° apart from each other around the cylindrical body portion 60. Since the splines 62 are spaced apart from each other, a slot 64 is formed between each pair of splines 64. A passageway (not shown) is formed through the carrier portion 54 which aligns with the passageway in the cannula 28 so that fluids can pass therethrough.

Figure 6:
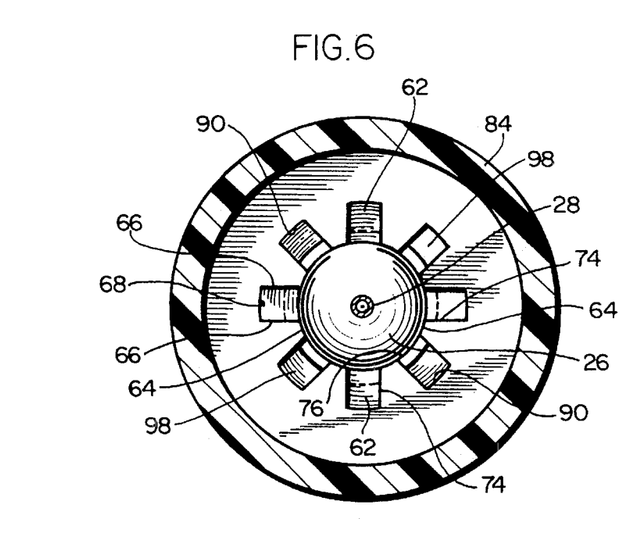
FIG. 6 is a cross-sectional view of the needle hub housing with the needle hub shown in elevation along line 6—6 of FIG. 4.

Each spline 62 on the hub 26 includes side walls 66 and a top wall 68. As shown in FIG. 6, the side walls 66 of the splines 62 are parallel to each other. The top wall 68 has a flat portion 70 which is perpendicular to the side walls 66 and a leading edge or nose 72 which tapers from the flat portion 70 to the cylindrical body portion 60 of the hub 26. The splines 62 extend along the length of the first body portion 60 from generally the front end of the body portion 60 to the second body portion 61. The top surface of the splines 62 lie flush with the top surface of the second body portion 61. The splines 62 provide strength to the overall assembly while permitting the use of reduced amount of plastic material in the assembly.

The slots 64 on the hub 26 have side walls 74 which are formed from the spline side walls 66 and a bottom wall 76 which is formed from the cylindrical body portion 60 of the carrier portion 54. The side walls 74 of the slots 64 radiate outwardly from the bottom wall 76 such that the bottom end of the slot 64 is narrower than the top end of the slot 64. The rear wall 78 of each slot 64 tapers upwardly from the bottom wall 76 of the slot 64 to the second cylindrical body portion 61.

As shown in FIG. 2, the second end of the carrier portion 54 has a generally annular projection 80 therearound. The annular projection 80 includes two ears 82 which project outwardly therefrom for connection to a conventional Luer lock fitting 36 in a manner well-known in the art.

The needle hub 26 and associated needle 28 are attached to the needle hub housing 30 to form the completed novel needle connector assembly or device 22 of the present invention. A first embodiment of the needle hub housing 30 is shown in FIGS. 1–6. A second embodiment of the needle hub housing 30 is shown in FIGS. 7–10. The general features of the housing 30 are first described with the specifics of the two embodiments described thereafter. Like elements in the first and second embodiments are designated by like reference numerals.

The housing 30 is a generally cylindrical, plastic, outer member 84 with an interior splined portion 86 generally at a second or rearward end of the housing 30. A first or forward end of the housing 30 is designed for engagement with the receptacle 24, and will be discussed hereinafter. The outer surface of the housing 30 has raised ribs or ridges 88 thereon for reasons described herein. The interior diameter of the cylindrical outer member 84 is larger than the exterior diameter of the second portion 42 of the receptacle 24 so that the second portion 42 of the receptacle 24 can be secured within the outer member 84. The exterior diameter of the first portion 40 of the receptacle 24 and the exterior diameter of the housing 30 are approximately equal for reasons described herein. The splined portion 86 in the rearward portion of housing 30 mates with the male splines 62 and slots 64 on the hub 26 to interconnect the hub 26 and the housing 30 together.

The splined portion 86 of the housing 30 includes a plurality of equi-spaced grooves or slots 90 which are separated from each other by a plurality of equi-spaced splines 92. Preferably, the slots 90 are spaced 45° from each other around the circumference of the housing 30.

The slots 90 in the housing 30 are generally complementarily shaped to the splines 62 on the hub 26. As such, each slot 90 has parallel side walls 94 and a bottom wall 96. When the hub 26 is inserted into the housing 30, the slots 90 in the housing 30 mate with the male splines 62 on the hub 26.

Figure 5:
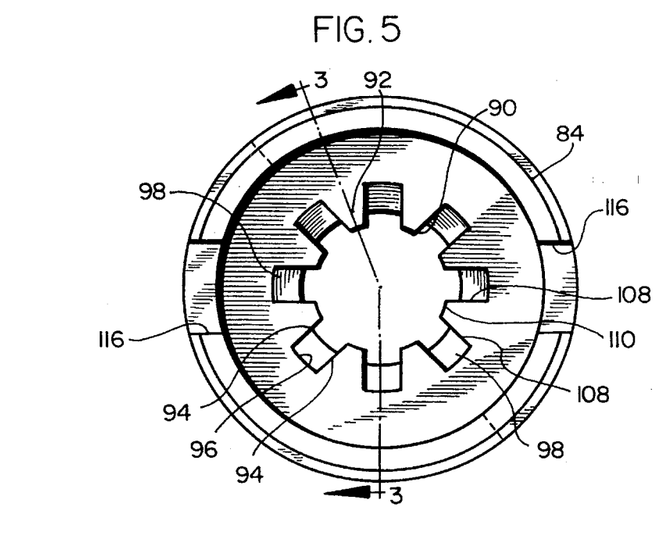
FIG. 5 is a front elevational view of the needle hub housing and needle hub shown along line 5—5 of FIG. 3.

Each slot 90 in the housing 30 has an inwardly projecting, one-way barb 98 formed in the bottom wall 96 along its length rearward of the leading edges of the splines 92. Each barb 98 has an inclined or cam surface 100 along its leading edge, a generally flat top surface 102 and a rearward surface 104 which is approximately 90° relative to the top surface 102 at its following edge. The cam surface 100 is inclined, at an angle of from 2°–45° with 32° being preferred, which angle is measured relative to the horizontal slot 90 in the housing 30 and to the top surface 102 of the barb 98. The inclined or cam surface 100 permits and facilitates insertion of the male spline 62 of the hub 28 into the slot 90, with the barb 98 biting into the male spline 62 to preclude withdrawal of the hub 26 from the housing 30. As shown in FIG. 5, the barbs 98 are shorter than the splines 92 to permit insertion of the hub 28 into the housing 30. The plastic material of the hub 26 and its associated splines 62 is selected to be softer than that of the housing 30 and its barbs 98. As such, the splines 62 will be deformed slightly upon insertion, but due to the memory of the plastic material from which the hub 26 and the splines 62 are formed, the plastic material of the spline 62 will flow back around the barb 98, firmly to lock the housing 30 to the hub 26, and prevent withdrawal of the hub 26 from the connector housing 30. By way of example, the hub 26 and its associated splines 62 can be fabricated from a polypropylene or polyethylene material, while the housing 30 and barbs 98 may be fabricated from a styrenic plastic or a polycarbonate plastic material.

The splines 92 in the housing 30 are generally complimentarily shaped to the slots 64 on the hub 30. As such, each spline 92 has side walls 108 which radiate inwardly from the outer housing portion 84 to a generally flat bottom wall 110. Thus, the spline 92 is wider at its base end than at its terminus end. As shown in FIG. 3A, the leading edge or nose 112 of each spline 92 is blunt and rounded for easy insertion of the needle hub 26 into the housing 30 as described herein. When the needle hub 26 is inserted into the housing 30, the splines 92 in the housing 30 mate with the slots 64 in the hub 26.

When the hub 26 is properly inserted into the housing, the male splines 62 of the hub 26 sit within the slots 90 in the housing 30. If during the insertion procedure, the splines 62 on the hub 26 do not align with the slots 90 in the housing 30, the tapered leading edges 72 of the splines 62 on the hub 26 contact the blunt, rounded leading edges 112 of the splines 92 in the housing 30. Since the leading edge 112 of the splines 92 in the housing are blunt and rounded, the leading edges 112 of the splines 92 produce a slight relative rotation to guide the splines 62 on the hub 26 into a slot 90. Thus, if the splines 62 on the hub 26 are not properly aligned with slots 90 in the housing 30 and contact the splines 92 in the housing 30, the rounded leading edges 112 of the splines 92 will engage the tapered leading edges 72 of the splines 62 on the hub 26 and cause the hub 26 to "rachet" until the hub 26 is properly aligned with the housing 30. While the leading edges 72 of the splines 62 on the hub 26 are disclosed as tapered and the leading edges 112 of the splines 92 in the housing 30 are disclosed as blunt and rounded, it is within the scope of the invention that the leading edges 72 of the splines 62 on the hub 26 be blunt and rounded and the leading edges 112 of the splines 92 in the housing 30 be tapered.

After the splines 62 have properly entered slots 90, the hub 26 is forced into the housing 30 so that the splines 62 slide along the length of the slots 90 and over the one-way barbs 98 until the rounded leading edges 112 of each spline 92 abuts against the tapered rear walls 78 of each respective slot 64. The engagement of the leading edges 112 of the splines 92 with the rear walls 78 of the slots 64 acts as a stop to prevent the hub 26 from entering any further into the housing 30.

As shown in FIGS. 4 and 9, as each spline 62 passes over a barb 98, the plastic material of the spline 62 deforms around the barb 98 and flows around the barb 98. This results in a slightly enlarged, rounded portion 114 proximate to the barb 98. The plastic of the hub 26 has sufficient memory to deform and flow around the barb 98 and to form a tight, secure fit between the hub 26 and the housing 30. Once the spline 62 has passed over the barb 98, the barb 98 bites into or embosses the spline 62 which "creeps" into tighter engagement over the time, resulting in push out forces of 15 to 25 pounds for the hub 26 to be removed from the housing 30. As shown in FIG. 6, the splines 92 on the housing 30 frictionally fit and abut against the slots 64 in the hub 26 to effectively lock the splines 92 and the slots 64 together. The cannula or needle 28 is surrounded by and encapsulated within the housing 30 so that there is minimal danger to a nurse or a technician from being inadvertently punctured by the needle 28 either before or after use of the connector device 22.

Figures 7, 8, 10:
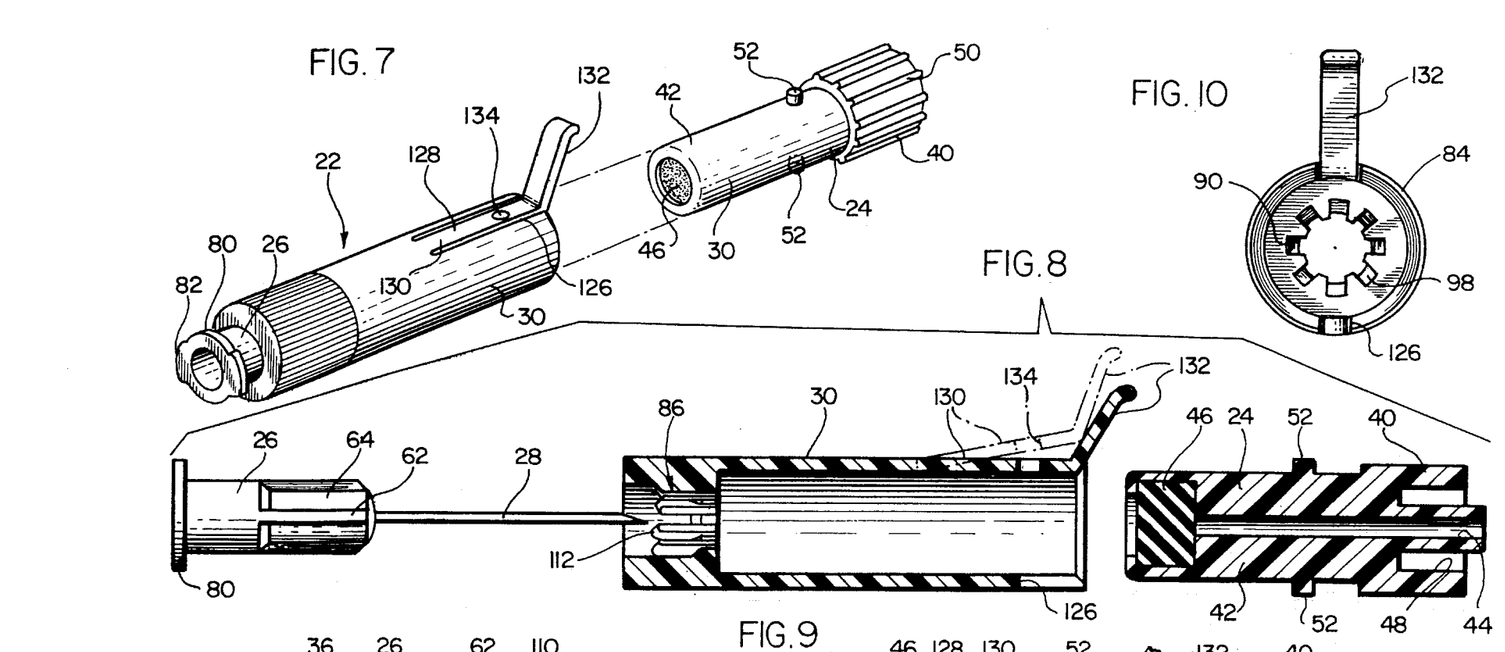
FIG. 7 is a perspective, partially exploded view of a needle connector assembly which incorporates the features of a second embodiment of the invention.
FIG. 8 is an exploded view of the needle connector assembly shown in FIG. 7 which is formed of a needle hub; a needle hub housing and a needle site receptacle; the needle hub housing and receptacle being shown in a cross-sectional view and the needle hub being shown in side elevation.
FIG. 10 is a front elevational view of the needle hub housing shown in FIG. 7.

As shown in FIGS. 5 and 10, the housing 30 has eight slots 90 therein. Since the slots 90 in the housing 30 are at 45° apart from each other and the splines 62 on the hub 26 are 90° apart from each other, the splines 62 on the hub 26 easily align with the slots 90 in the housing 30. The splines 62 on the hub 26 engage four of the eight slots 90 provided in the housing 30. It is not critical as to which way the hub 26 is turned relative to the housing 30.

While the present invention is disclosed with the slots 90 in the housing 30 having the barbs 98 therein, it is envisioned that the splines 92 in the housing 30 could instead have the barbs thereon. If barbs are provided on the splines 92, the barbs are formed in the same manner as the barbs 98. The leading edge of the barb on the spline 92, viz. the edge which would first come into contact with the hub 26, would have the cam surface thereon. The barb on the spline 92 would bite into the slot 64 on the hub 26. Alternatively, the needle hub 26 could instead have barbs thereon along the length of the slots 64 or on the splines 62. Of course, if barbs are provided on the hub 26, they are disposed oppositely of barbs 98 on the housing 30. The leading edge of the barb, viz. the edge which would first come into contact with the housing 30 would have the cam surface thereon. If a barb is provided on the slot 64 on the hub 26, the barb bites into the respective spline 92 on the housing 30. If a barb is provided on the spline 62 on the hub 26, the barb bites into the respective slot 90 on the housing 30. Also, means other than the one-way-type barbs as discussed above could be used to maintain assembly of the needle hub 26 when engaged through an aperture in the rear portion of housing 30 such as a tapered wedge lock, gluing or ultrasonic welding.

After the needle hub 26 has been inserted into the housing 30 to form the completed novel needle connector device 22 of the present invention, the device 22 is affixed to the patient by attaching and interlocking the connector assembly device 22 to the receptacle 24. Two embodiments for interlocking the device 22 to the receptacle 24 are disclosed herein. Since the exterior surface of the housing 30 and the first portion 40 of the receptacle 24 are ridged, a nurse or technician can easily grasp the members 24, 30 and manipulate the members 24, 30 as described herein.

Directing attention to FIGS. 1–6, the first embodiment of the housing 30 includes a bayonet twist lock for securely interconnecting the assembled device 22 and the needle site receptacle 24 together. Two bayonet slots 116 are provided in the first end of the housing 30 and are diametrically opposed to each other along the circumference of the housing 30. Each bayonet slot 116 is generally L-shaped and has a first portion 118 which is generally collinear with the center line of the housing 30 and a second portion 120 which is generally perpendicular to the center line of the housing 30 and to the first portion 118 of the bayonet slot 116. The first and second portions 118, 120 of the slot 116 define a corner 122 in the housing 30 at the juncture between the portions 118, 120. To assemble the receptacle 24 and the housing 30 together, each pin 52 on the receptacle 24 is inserted within its respective bayonet slot 116 on the housing 30. The first and second portions 118, 120 of each bayonet slot 116 are approximately the same width as the diameter of the pin 52 on the receptacle 24. Each bayonet slot 116 has a restricted throat portion 124 along the second portion 120 of the slot 116 to hold the pin 52 securely within the slot 116. The restricted portion 124 of the bayonet slot 116 has a width which is slightly smaller than the diameter of the pin 52.

To assemble the receptacle 24 and the housing 30 together, the housing 30 is pushed over the receptacle 24 and twisted to secure the housing 30 and the receptacle 24 together. During the push in motion, the second portion 42 of the receptacle 24 enters into the first end of the housing 30 and the housing 30 is rotated until each pin 52 aligns with a bayonet slot 116. The pin 52 is inserted into its respective bayonet slot 116 and slides along the first portion 118 of the slot 116 until the pin 52 contacts the end of the first portion 118. The first, larger portion 40 of the receptacle 24 will abut against the first end of the housing 30 when the pin 52 is properly pushed in since it is approximately the same diameter as the housing 30 and thus cannot enter into the housing 30. This aids a nurse or technician in deciding whether the receptacle 24 has been fully inserted into the housing 30. As the housing 30 is pushed over the receptacle 24, the tip 58 of the needle 28 penetrates the rubber plug 46 and as the housing 30 is pushed further, the needle 28 penetrates completely through the rubber plug 46. Once the needle 28 penetrates through the plug 46, the plug 46 seals around the needle 28 and fluids can pass through the connection. Since the plug 46 seals around the needle 28, a sealed connection is provided between the receptacle 24 and the device 22.

During the twist motion, the housing 30 is rotated by the nurse or technician relative to the receptacle 24 and each pin 52 travels along the second portion 120 of the bayonet slot 116 until the pin 52 reaches the end of the second portion 120. The pin 52 passes beyond the restricted throat portion 124 of the bayonet slot 116 by deforming the plastic material of the housing 30 to allow the pin 52 to pass therethrough. The plastic of the housing 30 has memory to deform and then return to its initial shape to securely hold the pin 52 beyond the restricted portion 124 of the slot 116.

The L-shape of the bayonet slots 116 minimize the possibility of the housing 30 and the receptacle 24 from becoming inadvertently detached from each other since the pin 52 must travel around the corner 122 in the slot 116. It is envisioned, however, that the slot could be instead a straight slot that has a restricted throat portion along its length behind which the pin is captured to securely lock the housing and the receptacle together. While two bayonet slots 116 are shown and described, it is to be understood that more than two slots 116 may be provided to correspond to the number of pins 52 provided on the receptacle 24.

To remove the housing 30 from the receptacle 24, the opposite motion is performed by the nurse or technician. First the housing 30 is rotated so that the pin 52 on the receptacle 24 passes the opposite way past the restricted throat portion 124 on the housing 30. Thereafter, the housing 30 is pulled outwardly from the receptacle 24. As the housing 30 is pulled outwardly from the receptacle 24, the needle or cannula 28 is pulled outwardly from the plug 46. Once the housing 30 has been completely removed from the receptacle 24, the needle or cannula 28 is also completely removed from the plug 46 in the receptacle 24. Since the plug 46 is rubber, the plug 46 reseals itself and fluids cannot pass through the receptacle 24.

Now directing attention to FIGS. 7–10, the second embodiment of the housing 30 includes a "lift latch" for interconnecting the assembled device 22 to the needle site receptacle 24. Two straight slots 126 are provided in the first end of the housing 30 and are diametrically opposed to each other along the circumference of the housing 30. Each straight slot 126 is generally collinear with the center line of the housing 30 and are slightly larger than the diameter of the pins 52 on the receptacle 46.

A latch 128 overlays one of the slots 126 and is same width as the slot 126. The latch 128 can be lifted away from the cylindrical portion 84 of the housing 30 to expose the slot 126. The latch 128 has a first portion 130 which overlays the slot 126 and a second free portion 132 which a nurse or technician can grasp to lift the latch 128 upwardly from the cylindrical portion 84 of the housing 30. The first portion 130 of the latch 128 has an aperture 134 thereon which is generally the same size as the pin 52 on the receptacle 24 for reasons described herein.

To assemble the receptacle 24 and the housing 30 together, the latch 128 is lifted away from the cylindrical portion 84 of the housing 30 to expose the slot 126. The housing 30 is inserted over the second portion 42 of the receptacle 24 so that the second end of the receptacle 24 is inserted into the first end of the housing 30. The housing 30 is rotated until each pin 52 is aligned with one of the straight slots 126 on the housing 30. Thereafter, the housing 30 is pushed over the receptacle 30 and the pins 52 slide along their respective slots 126 until the end of the first, larger portion 40 of the receptacle 24 abuts against the first end of the housing 30. Since the first portion 40 of the receptacle 24 is approximately the same diameter as the housing 30, the first portion 40 cannot enter into the housing 30 which aids a nurse or technician in deciding whether the housing 30 and receptacle 24 are properly assembled together. When the housing 30 properly overlays the receptacle 24, the needle 28 penetrates completely through the rubber plug 46 in the receptacle 24 and thus, fluids can pass through the connection. The rubber plug 46 seals around the needle 28 and a sealed connection is formed between the receptacle 24 and the device 22. Thereafter, the latch 128 is moved towards the cylindrical housing 30 to overlay the slot 126. The pin 52 is inserted into and captured within the aperture 134 in the latch 128 to securely hold the housing 30 and the receptacle 24 together.

To remove the housing 30 from the receptacle 24, the latch 128 is lifted upwardly to free the pin 52 from the aperture 134. Thereafter, the housing 30 is pulled outwardly from the receptacle 24. As the housing 30 is pulled outwardly from the receptacle 24, the needle or cannula 28 is pulled outwardly from the plug 46. Once the housing 30 has been completely removed from the receptacle 24, the needle 28 is also completely removed from the plug 46 in the receptacle 24. Since the plug 46 is rubber, the plug 46 reseals itself and fluids cannot pass through the receptacle 24. While one latch 128 is disclosed herein, it is to be understood that latches may be provided for both slots 126 on the housing 30.

While preferred embodiments of the present invention are shown and described, it is envisioned that those skilled in the art may devise various modifications of the present invention without departing from the spirit and scope of the appended claims. The invention is not intended to be limited by the foregoing disclosure.

The invention claimed is:

1. A needle connector assembly for use in administering intravenous fluids to a patient comprising: a needle hub; a housing; one of said needle hub or said housing having a plurality of equi-spaced splines thereon; the other of said needle hub or said housing having a plurality of equi-spaced slots thereon; said splines interengaging with said slots when said needle hub is inserted into said housing; barb means on said interengaged splines and slots for precluding withdrawal of the needle hub from the housing when the needle hub is inserted into said housing.

2. A needle connector assembly as defined in claim 1, wherein said barb means comprises a barb having a cam surface thereon to permit insertion of said needle hub into said housing.

3. A needle connector assembly as defined in claim 1, wherein said slots are on said housing and said barb means are provided along the length of each slot on said housing.

4. A needle connector assembly as defined in claim 1, wherein said splines are on said housing and said barb means are provided along the length of each spline on said housing.

5. A needle connector assembly as defined in claim 1, wherein said slots are on said needle hub and said barb means are provided along the length of each slot on said needle hub.

6. A needle connector assembly as defined in claim 1, wherein said splines are on said needle hub and said barb means are provided along the length of each spline on said needle hub.

7. A needle connector assembly as defined in claim 1, wherein said slots are on said housing and said splines are on said needle hub, said housing further including a plurality of splines thereon which alternate with said slots on said housing, said needle hub further including a plurality of slots thereon which alternate with said splines on said needle hub.

8. A needle connector assembly as defined in claim 7, wherein one of said splines on said housing or said needle hub have a rounded leading edge, each said rounded leading edge mating with a leading edge of the other of said splines on said housing or said needle hub to facilitate entry of said splines on said needle hub into said slots on said housing.

9. A needle connector assembly as defined in claim 8, wherein said leading edge on said other of said splines on said housing or said needle hub are tapered.

10. A needle connector assembly as defined in claim 1, wherein said housing has at least one slot thereon at an end opposite to which the needle hub is engaged, and further including a needle site receptacle which comprises a cylindrical member having at least one pin projecting outwardly therefrom, said pin being inserted within said slot to connect the housing and the needle site receptacle together.

11. A needle connector assembly as defined in claim 10, wherein said slot has a restricted portion which has a width which is slightly smaller than the diameter of the pin such that when said pin is inserted into said slot to connect the housing and the needle site receptacle together, said pin passes beyond the restricted portion in said slot.

12. A needle connector assembly as defined in claim 10, wherein said housing further includes a latch which overlays said slot, said latch having an aperture therein and being movable generally away from said cylindrical member to expose said slot, said latch being movable towards said housing to capture said pin within said aperture in said latch when said housing and said needle site receptacle are assembled together.

13. A method of assembling a needle connector assembly for use in administering intravenous fluids to a patient comprising providing a needle hub and a housing, one of said needle hub or said housing having a plurality of equi-spaced splines thereon, the other of said needle hub or said housing having a plurality of equi-spaced slots thereon, barb means provided on at least one of said splines or said slots; inserting said needle hub into said housing to align said splines with said slots, advancing said needle hub into said housing, said barb means precluding withdrawal of the needle hub from the housing.

14. A method as defined in claim 13, wherein said slots are on said housing and said barb means are provided along the length of each slot on said housing.

15. A method as defined in claim 13, wherein said splines are on said housing and said barb means are provided along the length of each spline on said housing.

16. A method as defined in claim 13, wherein said slots are on said needle hub and said barb means are provided along the length of each slot on said needle hub.

17. A method as defined in claim 13, wherein said splines are on said needle hub and said barb means are provided along the length of each spline on said needle hub.

18. A method as defined in claim 13, further including the step of securing a needle site receptacle to said assembled needle hub and said housing.

19. A method as defined in claim 18, wherein said housing comprises a generally cylindrical member having at least one slot thereon, and said needle site receptacle comprises a cylindrical member having at least one pin projecting outwardly therefrom, said slot having a restricted portion which has a width which is slightly smaller than the diameter of said pin; and wherein said step of securing the needle site receptacle to said assembled needle hub and said housing comprises inserting the pin into the slot such that the pin passes beyond the restricted portion in said slot to securely hold the pin within the slot.

20. A method as defined in claim 18, wherein said housing comprises a generally cylindrical member having at least one slot thereon and at least one latch thereon which overlays the slot, said latch having an aperture therein and being movable generally away from said cylindrical member to expose the slot in said housing, and said needle site receptacle comprises a cylindrical member having at least one pin projecting outwardly therefrom, and wherein said step of securing the needle site receptacle to said assembled needle hub and said housing comprises lifting said latch upwardly and inserting said pin into said slot on said housing and thereafter moving said latch towards said housing and capturing said pin within said aperture in said latch.

21. A needle connector assembly for connection to an IV receptacle for use in administering intravenous fluids to a patient, comprising: a needle carrying hub; a housing having a forward end portion for receiving said receptacle and an apertured rear portion; said needle carrying hub and said aperture in the rear portion of said housing being of complimentary shape, with said needle carrying hub being fixedly engaged in said housing aperture, and structure for maintaining the assembly of said needle carrying hub within said housing aperture and for substantially preventing removal of said needle carrying hub from said housing aperture, with said needle disposed within and shielded by said housing.

22. A needle connector assembly according to claim 21, wherein said complimentary shaped needle hub and said aperture include at least one interengagable spline and slot.

23. A needle connector assembly according to claim 22, wherein said structure for maintaining the assembly of said needle carrying hub within said housing aperture and for substantially preventing removal of said needle carrying hub from said housing aperture includes at least one one-way barb formed on one or the other of said spline or slot.

24. A needle connector assembly according to claim 23, wherein a plurality of interengagable splines and slots are provided, with one-way barbs formed on one or the other of said splines or slots.

25. A needle connector assembly according to claim 21, wherein said needle carrying hub extends from the rear portion of the housing and includes means for affixing an IV fluid supply line thereto, such that once the needle connector assembly is connected to a recptacle, the IV fluid will pass from said supply line into said hub and force said needle in to said receptacle, without there being provided a fluid interface involving said housing.

26. A method of assembling a needle connector assembly for connection to a receptacle for use in administering intravenous fluids to a patient, comprising the steps of: providing a needle hub and a housing, with said housing having a forward end for receiving said receptacle, and an aperture in the rear portion of said housing, with said needle hub having a shape complimentary to said aperture in the rear portion of said housing; inserting said needle hub into said housing through said aperture in the rear portion thereof; advancing said needle hub into said housing to attain a desired, seated position; and providing structure operatively associated with said needle hub and the rear portion of said housing for maintaining said needle hub in the desired, seated position and to substantially prevent withdrawal of said needle hub from said seated position from within said housing.

27. A method according to claim 26, wherein the step of providing structure associated with the needle hub and the rear portion of the housing for maintaining the desired, seated position and for substantially preventing withdrawal of said needle hub from said seated position, includes the step of forming said needle hub and said aperture in the rear portion of said housing with interchangeable splines and slots.

28. A method according to claim 27, further including the provision of one-way barbs on one of said splines or slots which engage the material of the other of said splines or slots, with the memory of the plastic of said engaged member causing said material to be deformed and return flow over said one-way barbs.

29. A needle connector assembly for connection to an IV receptacle for use in administering intravenous fluids to a patient, comprising: a needle carrying hub; a housing having a forward end portion for receiving said receptacle and an apertured rear portion; said needle carrying hub and said aperture in the rear portion of said housing being of complimentary shape and including at least one interengagable spline and slot, with said needle carrying hub being fixedly engaged in said aperture, and means for maintaining said assembly of said needle carrying hub within said housing aperture including at least one one-way barb formed on one or the other of said spline or slot, with said needle disposed within and shielded by said housing.

30. A needle connector assembly according to claim 23, wherein there is provided a plurality of interengagable splines and slots, with one-way barbs formed on one or the other of said splines or slots.

31. A method of assembling a needle connector assembly for connection to a receptacle for use in administering intravenous fluids to a patient, comprising the steps of:

providing a needle hub and a housing, with said housing having a forward end for receiving said receptacle, and an aperture in the rear portion of said housing, with said needle hub having a shape complimentary to said aperture in the rear portion of said housing;

inserting said needle hub into said housing through said aperture in the rear portion thereof; advancing said needle hub into said housing to attain a desired, seated position; and providing means operatively associated with said needle hub and the rear portion of said housing for maintaining said needle hub in the desired, seated position and to resist withdrawal of said needle hub from said housing by forming said needle hub and said aperture in the rear portion of said housing with interchangeable splines and slots, one of said splines or slots being provided with one-way barbs which engage the material of the other of said splines or slots, with the memory of the plastic of said engaged member causing said material to be deformed and return flow over said one-way barbs.

* * * * *